(12) United States Patent
Drent et al.

(10) Patent No.: US 7,414,155 B2
(45) Date of Patent: Aug. 19, 2008

(54) PROCESS FOR THE HYDROFORMYLATION OF AN ETHYLENICALLY UNSATURATED COMPOUND

(75) Inventors: Eit Drent, Amsterdam (NL); Roelof Van Ginkel, Amsterdam (NL); Willem Wabe Jager, Amsterdam (NL)

(73) Assignee: Shell Oil Company, Houston, TX (US)

( * ) Notice: Subject to any disclaimer, the term of this patent is extended or adjusted under 35 U.S.C. 154(b) by 23 days.

(21) Appl. No.: 11/759,623

(22) Filed: Jun. 7, 2007

(65) Prior Publication Data

US 2007/0238892 A1 Oct. 11, 2007

Related U.S. Application Data

(62) Division of application No. 10/670,105, filed on Sep. 24, 2003, now Pat. No. 7,250,538.

(30) Foreign Application Priority Data

Sep. 26, 2002 (EP) .................. 02256696

(51) Int. Cl.
C07F 9/02 (2006.01)
C07F 7/08 (2006.01)
(52) U.S. Cl. .......................... 568/12; 556/21
(58) Field of Classification Search .............. 568/12
See application file for complete search history.

(56) References Cited

U.S. PATENT DOCUMENTS

| | | | |
|---|---|---|---|
| 2,042,011 A | 5/1936 | Loomis | 166/21 |
| 5,189,003 A | 2/1993 | Klusener et al. | 502/167 |
| 5,780,684 A | 7/1998 | Drent et al. | 568/454 |
| 5,817,848 A | 10/1998 | Kamer et al. | 556/12 |
| 5,874,600 A * | 2/1999 | Rautenstrauch et al. | 556/136 |
| 5,994,591 A | 11/1999 | Arnoldy et al. | 568/454 |
| 6,037,500 A | 3/2000 | Zhang | 568/12 |
| 6,103,927 A | 8/2000 | De Castro Loureiro Barreto Rosa et al. | 560/207 |
| 6,156,936 A | 12/2000 | Drent et al. | 568/454 |
| 6,290,926 B1 | 9/2001 | Haenel et al. | 423/437.2 |
| 6,455,460 B1 * | 9/2002 | Dobbs et al. | 502/155 |
| 6,525,210 B1 * | 2/2003 | Zhang et al. | 556/21 |
| 6,613,922 B2 | 9/2003 | Zanotti-Gerosa et al. | 556/19 |
| 6,806,378 B2 * | 10/2004 | Tucker et al. | 556/137 |
| 6,828,271 B2 * | 12/2004 | Zhang et al. | 502/162 |
| 6,835,850 B2 * | 12/2004 | Drent et al. | 560/207 |
| 7,098,369 B2 | 8/2006 | Drent et al. | 568/881 |
| 7,105,689 B2 | 9/2006 | Slany et al. | 556/18 |
| 2003/0163003 A1 * | 8/2003 | Zhang et al. | 564/489 |
| 2004/0059157 A1 | 3/2004 | Slany et al. | 564/16 |
| 2004/0220049 A1 | 11/2004 | Hems et al. | 502/150 |

FOREIGN PATENT DOCUMENTS

| | | |
|---|---|---|
| DE | GE10106348 | 8/2002 |
| EP | 0495547 A2 | 1/1992 |
| EP | 0499329 | 5/1994 |
| EP | 0900776 A1 | 3/1999 |
| EP | 0922691 A1 | 6/1999 |
| FR | 2671132 | 7/1992 |
| GB | 2306344 | 5/1997 |
| JP | 2002513376 | 8/2002 |
| WO | WO 95/05354 | 2/1995 |
| WO | WO9530680 | 11/1995 |
| WO | WO0114299 | 3/2001 |
| WO | WO 01/87899 A1 | 11/2001 |
| WO | WO 02/26690 A1 | 4/2002 |
| WO | WO0236261 | 5/2002 |
| WO | WO022057278 | 7/2002 |
| WO | WO 02/064250 A2 | 8/2002 |

OTHER PUBLICATIONS

"Hydroformylation of Internal Olefins to Linear Aldehydes with Novel Rhodium Catalysts," by Lars A. van der Veen, Paul C. J. Kramer, and Piet W. N. M. van Leeuwen, Angew. Chem. Int. Ed. 1999, 38 No. 3, pp. 336-338.

"On the Mechanism of the Thermal Tetramerization of Phospholes," by M. O. Bevierre, F. Mercier, L. Richard, and F. Mathey, Bulletin de la Societe Chimique de France (1992), 129, 1-8.

"Versatile Ligands for Palladium-Catalyzed Asymmetric Allylic Alkylation," by Peter Dierkes, Shailesh Ramdeehul, Laurent Barloy, Andre De Cian, Jean Fischer, Paul C. J. Kamer, Piet W. N. M. van Leeuwen, and John A. Osborn, Angewandte Chemie, International Edition (1998), 37, No. 22, pp. 3116-3118.

Chemical Abstracts Service, Waschbuesch, Klaus et al., "Combining the Chemistry of Phospholes and Phosphinines," Data accession No. 124:176301, abstract of Bulletin de la Societe Chimique de France (1995), 132(9), 910-19.

"Palladium-Catalyzed Enantioselective Multiple Carbonylation of 1-Olefins. Syntesis of Optically Active 2-oxo-pentanedioates and Butanedioates," by Martin Sperrle, Giambattista Consiglio, Inorganic Chimica Acta (2000) pp. 264-272.

Chemical Abstracts Service, Fujie, Naoto et al., "Asymmetric Reactions Catalyzed by Chiral Metal Complexes. LXXXV. Synthesis of new Atropisomeric Bisphosphine Ligands Bearing Chiral Phospholane and Their use in Asymmetric Hydrogenation," Database accession No. 130:296749, abstract of Chemical & Pharmaceutical Bulletin (1999) 47(3), pp. 436-439.

* cited by examiner

Primary Examiner—Yvonne Eyler
Assistant Examiner—Louisa Lao

(57) ABSTRACT

Process for the hydroformylation of an optionally substituted ethylenically unsaturated compound by reaction thereof with carbon monoxide and hydrogen in the presence of a specific catalyst system which includes a source of Group VIII metal cations; a diphosphine ligand having the general formula (I):

$$X^1\text{---}R\text{---}X^2 \qquad (I)$$

wherein $X^1$ and $X^2$ each independently represent an optionally substituted cyclic group with at least 5 ring atoms, of which one is a phosphorus atom, and R represents a bivalent optionally substituted bridging group which is connected to each phosphorus atom by a $sp^2$ hybridized carbon atom; an acid having a $pK_a < 3$; and a source of halide anions.

2 Claims, No Drawings

PROCESS FOR THE HYDROFORMYLATION OF AN ETHYLENICALLY UNSATURATED COMPOUND

This is a division of application Ser. No. 10/670,105 filed Sep. 24, 2003, now U.S. Pat. No. 7,250,538 the entire disclosure of which is hereby incorporated by reference.

FIELD OF THE INVENTION

The present invention relates to a process for the hydroformylation of an ethylenically unsaturated compound by reaction thereof with carbon monoxide and hydrogen in the presence of a catalyst system.

BACKGROUND OF THE INVENTION

Such processes are known in the art from for example WO-A-9505354, EP-A-0495547 and WOA-01/67899. Although good activities towards a hydroformylation product are obtained, there is still room for improvement, especially when larger ethylenically unsaturated compounds are hydroformylated. It is furthermore desirable to provide such a hydroformylation process where high activities towards a hydroformylation product can be obtained when the process is carried out under acidic conditions.

WO-A-01/87899 relates amongst others to the carbonylation of ethylenically unsaturated compounds. It describes a specific class of bidentate diphosphines. The phosphorus atoms in these diphosphines are connected by a bridging group. A wide range of bridging groups is described. Cyclopentene is mentioned in passing as a possible bridging group. However, no bidentate diphosphines comprising a cyclopentene bridge are mentioned. Furthermore it is not indicated how such a cyclopentene bridge should be connected to the phosphorus atoms.

WO-A-0226690 relates to a process for the carbonylation of conjugated dienes. The examples describe the reaction of 1,3-butadiene and methanol to methyl-pentenoate in the presence of a catalyst comprising palladium acetate, a bidentate diphosphine and a carboxylic acid. Several bidentate diphosphines are exemplified. The examples show that, for the exemplified reaction with methanol, a catalyst system comprising 1,2-P,P'bis(9-phosphabicyclononyl) benzene as a bidentate diphosphine has only a moderate activity (400 mol/mol/hr), much lower than a catalyst system comprising R,S-meso-2,3-P,P'bis(9-phosphabicyclononyl)butane as a bidentate diphosphine (560 mol/mol/hr).

SUMMARY OF THE INVENTION

It has now surprisingly been found that when a specific bidentate diphosphine, such as for example 1,2-P,P'bis(9-phosphabicyclononyl) benzene, is used in a catalyst for a hydroformylation reaction, especially a hydroformylation reaction under acidic conditions, unexpected advantages with regard to the activity towards a hydroformylation product are obtained.

Accordingly the present invention provides a process for the hydroformylation of an optionally substituted ethylenically unsaturated compound by reaction thereof with carbon monoxide and hydrogen in the presence of a catalyst system comprising:

(a) a source of Group VIII metal cations;

(b) a diphosphine ligand having the general formula (I):

$$X^1\text{—}R\text{—}X^2 \qquad (I)$$

wherein $X^1$ and $X^2$ each independently represent an optionally substituted cyclic group with at least 5 ring atoms, of which one is a phosphorus atom, and R represents a bivalent optionally substituted bridging group which is connected to each phosphorus atom by a $sp^2$ hybridized carbon atom;

(c) an acid having a $pK_a<3$, measured in an aqueous solution at 18° C., or a salt derived therefrom; and (d) a source of halide anions.

$sp^2$ is the hybridization at carbon atoms. A tetrahedral C, such as in paraffins, has $sp^3$ hybridization. A carbon atom involved in a double bond has $sp^2$ hybridization, as in ethylene. A carbon involved in an acetylenic bond has a sp hybridization, such as in alkynes.

DETAILED DESCRIPTION OF THE INVENTION

The process of the present invention is specifically directed to the hydroformylation of ethylenically unsaturated compounds, which shows specific reaction characteristics when compared to carbonylation reactions in general. The advantages are furthermore especially pronounced when the ethylenically unsaturated compound is a large compound, i.e. comprising at least 4 carbon atoms and preferably at least 6 carbon atoms. Advantageously high reaction rates towards a hydroformylation product can furthermore be obtained under acidic conditions. Such acidic conditions help stabilize the catalyst by decreasing the risk of reduction of the Group VIII metal cation.

R represents a bivalent optionally substituted bridging group which is connected to each phosphorus atom by an $sp^2$ hybridized carbon atom Both phosphorus atoms can be connected to one and the same $sp^2$ hybridized carbon atom. Preferably, however, R comprises at least two $sp^2$ hybridized carbon atoms and each phosphorus atom is connected to a separate $sp^2$ hybridized carbon atom.

Preferably R represents a bivalent optionally substituted bridging group comprising 2 or more atoms in the bridge. By "a bridge" is understood to be the shortest connection between both phosphorus atoms. More preferably R contains 2 to 6 atoms in the bridge, and most preferably R contains 2 to 4 atoms in the bridge. Especially preferred are those bridging groups R which contain 2 or 3 atoms in the bridge. Of these bridge atoms, preferably at least 2 are carbon atoms. More preferably all bridge atoms are carbon atoms. Most preferably R represents a bivalent optionally substituted bridging group connecting the phosphorus atoms via a bridge consisting of two $sp^2$ hybridized carbon atoms.

The bridging group R can be any group comprising at least one and preferably two $sp^2$ hybridized carbon atoms. Examples of such groups include alkene, cycloalkene and aromatic groups, wherein the carbon atom(s) connected to a phosphorus atom are connected via an unsaturated bond to another atom.

Examples of suitable alkene groups include alkene groups having more than 2 carbon atoms, more preferably from 2 to 10 carbon atoms, and most preferably from 2 to 6 carbon atoms. Especially preferred are alkene groups having 2 to 4 carbon atoms and more preferably alkene groups having 2 carbon atoms. The alkene group can contain heteroatoms such as N, O, P or S, either in the carbon chain or attached as a substituent to the carbon chain. The alkene group can contain one or more unsaturated bonds. The group can be a straight chain alkene group or a branched alkene group but is preferably a straight chain alkene group. The alkene group can have substituent groups attached to it containing heteroatoms such as N, O, P or S, alkyl groups or aryl groups.

Preferably such a substituent is an alkyl or aryl group, more preferably an alkyl or aryl group comprising from 1 to 6, more preferably from 1 to 4, carbon atoms, such as for example methyl, ethyl, n-propyl, isopropyl, n-butyl, iso-butyl or tert.-butyl and phenyl. Examples of suitable alkene groups include 1,2-vinylene (in IUPAC nomenclature 1,2-ethenylene); 1,2-diphenyl-1,2-vinylene; 1-methyl-1,2-vinylene; 1,2-dimethyl-1,2-vinylene; 1-methyl-2-ethyl-1,2-vinylene; 1,2-diethyl-1,2-vinylene; 1,3-(1,3-butadienyl)(in IUPAC nomenclature 1,2-dimethylene-1,2-ethylene); wherein the two free valencies are connected to the phosphorus atoms.

Examples of suitable cycloalkene groups include cycloalkene groups having more than 3 ring atoms, more preferably from 4 to 16 ring atoms, and most preferably from 5 to 10 ring atoms. Of these ring atoms at least two are $sp^2$ hybridized carbon atoms. The cycloalkene group can contain heteroatoms such as N, O, P or S, either in the carbon chain or attached as a substituent to the carbon chain. Preferably, however, the cycloalkene group only contains carbon atoms. The cycloalkene group can contain one or more unsaturated bonds, but preferably only contains one unsaturated bond. The cycloalkene group can have substituent groups attached to it containing heteroatoms such as N, O, P or S, alkyl groups or aryl groups. Preferably such a substituent is an alkyl or aryl group, more preferably an alkyl or aryl group comprising from 1 to 6, more preferably from 1 to 4, carbon atoms, such as for example methyl, ethyl, n-propyl, isopropyl, n-butyl, iso-butyl or tert.-butyl and phenyl. Most preferably, however, the cycloalkene group does not have substituent groups attached to it. Examples of suitable cycloalkene groups include 1-cyclopenten-1,2-ylene; 1-cyclohexen-1,2-ylene; 1-cyclohepten-1,2-ylene; 1-cyclo-octen-1,2-ylene; 3-methyl-1-cyclopenten-1,2-ylene; 1,3-cyclopenten-2,3-ylene; wherein the two free valencies are connected to the phosphorus atoms. Of these 1-cyclopenten-1,2-ylene and 1-cyclohexen-1,2-ylene are preferred.

Examples of suitable aromatic groups include monocyclic groups, such as for example a phenyl group, and polycyclic groups, such as for example naphthyl, anthryl or indyl groups. Preferably, however, the aromatic group is a monocyclic group. The aromatic group preferably has from 4 to 20 ring atoms, more preferably from 5 to 12 ring atoms and most preferably from 5 to 7 ring atoms. The aromatic group may contain just carbon atoms as ring atoms. Preferably, however, the aromatic ring also contains one or more heteroatoms, such as N, O, P or S, as a ring atom. Examples of suitable aromatic groups comprising one or more heteroatoms as a ring atom include for example pyridine, pyrrole, furan, thiophene, oxazole or thiazole groups. Preferred aromatic groups include thiophene and benzene. Optionally the aromatic group is substituted Suitable substituents include groups containing heteroatoms such as halides, sulphur, phosphorus, oxygen and nitrogen. Examples of such groups include fluoride, chloride, bromide, iodide and groups of the general formula —O—H, —O—$X^3$, —CO—$X^3$, —CO—O—$X^3$, —S—H, —S—$X^3$, —CO—S—$X^3$, —$NH_2$—$NHX^3$, —$NX^3X^4$, —$NO_2$, —CN, —CO—$NH_2$, —CO—$NHX^3$, —CO—$NX^3X^4$ and —$Cl_3$, in which $X^3$ and $X^4$, independently, represent alkyl groups having from 1 to 4 carbon atoms like methyl, ethyl, n-propyl, isopropyl, n-butyl, iso-butyl and tert.-butyl. If the aromatic group is substituted it is preferably substituted with one or more aryl, alkyl or cycloalkyl groups, preferably having from 1 to 10 carbon atoms. Suitable groups include, methyl, ethyl, propyl, iso-propyl, n-butyl, iso-butyl, tert.-butyl phenyl and cyclohexyl. Most preferably, however, the aromatic group is unsubstituted and only linked to the phosphorus atoms. Since the electrons of the double bond are delocalized in the aromatic ring structure, all aromatic carbon atoms of the ring are $sp^2$ hybridized. Hence, the phosphorus atoms can be connected via each combination of aromatic carbon atoms of the ring. Preferably, however, the phosphorus atoms are connected at adjacent positions, for example the 1 and 2 positions, of the aromatic group.

$X^1$ and $X^2$ represent a substituted or unsubstituted cyclic group with at least 5 ring atoms, of which one is a phosphorus atom, and preferably with from 6 to 12 ring atoms. The cyclic group can be a monocyclic group, such as for example a substituted or unsubstituted phosphacyclohexyl, phosphacycloheptyl or phosphacyclo-octyl group, or a polycyclic group. Preferably $X^1$ and/or $X^2$ represent a phosphabicycloalkyl group with at least 6 ring atoms, such as for example a 7-phosphabicycloheptyl, a 8-phosphabicyclooctyl or a 9-phosphabicyclononyl group. Most advantageously both $X^1$ and $X^2$ represent a substituted or unsubstituted 9-phosphabicyclononyl group. The 9-phosphabicyclononyl group can have several isomeric structures. For the purpose of the invention the [3,3,1] and [4,2,1] isomers are preferred. Suitably $X^1$ and $X^2$ are substituted or unsubstituted [3,3,1] or [4,2,1] 9-phosphabicyclononyl groups. The two 9-phosphabicyclononyl groups can have both the same or each a different isomeric structure. Most preferably the two 9-phosphabicyclononyl groups have the same isomeric structure, preferably the [3,3,1] isomeric structure.

One or both of the phosphacycloalkyl, or more preferably phosphabicycloalkyl, rings is suitably substituted with one or more suitable hydrocarbyl groups containing carbon atoms and/or heteroatoms. Suitable substituents include groups containing heteroatoms such as halides, sulphur, phosphorus, oxygen and nitrogen. Examples of such groups include fluoride, chloride, bromide, iodide and groups of the general formula =O, =S, —O—H, —O—$X^3$, —CO—$X^3$, —CO—O—$X^3$, —S—H, —S—$X^3$, —CO—S—$X^3$, —$NH_2$, —$NHX^3$, —$NX^3X^4$, —$NO_2$, —CN, —CO—$NH_2$, —CO—$NHX^3$, —CO—$NX^3X^4$ and —$Cl_3$, in which $X^3$ and $X^4$, independently, represent alkyl groups having from 1 to 4 carbon atoms like methyl, ethyl, n-propyl, isopropyl, n-butyl, iso-butyl and tert.-butyl. If a phosphabicyclononyl ring is substituted it is preferably substituted with one or more alkyl groups, preferably having from 1 to 10 carbon atoms, more preferably from 1 to 4 carbon atoms. Linear, branched or cyclic alkyl groups can be used. Suitable alkyl groups include, methyl, ethyl, propyl, iso-propyl, butyl and iso-butyl. More suitably methyl groups are used. The substituted phosphabicyclononyl ring can be mono- or poly-substituted and is preferably di-substituted. Most preferably the phosphabicyclononyl ring is substituted with two methyl groups.

Preferred bidentate ligands of formula (I) include all isomeric structures of 1,2-P,P'bis(9-phosphabicyclononyl) benzene;
1,2-P,P'bis(9-phosphabicyclononyl) 4-methyl benzene;
3,4-P,P'bis(9-phosphabicyclononyl) thiophene;
1,2-P,P'bis(9-phosphabicyclononyl)cyclopentene;
1,2-P,P'bis(9-phosphabicyclononyl)cyclohexene.

Of these, 3,4-P,P'bis(9-phosphabicyclo[3,3,1]nonyl) thiophene and 1,2-P,P'bis(9-phosphabicyclo[3,3,1]nonyl) cyclopentene are especially preferred.

Some of the above described diphosphine ligands are novel. Accordingly this invention also provides a diphosphine ligand having the general formula (II):

$$X^1-R^2-X^2 \quad (II)$$

wherein $X^1$ and $X^2$ each independently represent an optionally substituted cyclic group with at least 5 ring atoms, of which one is a phosphorus atom, and $R^2$ represents a bivalent optionally substituted bridging group which is connected to each phosphorus atom by a sp² hybridized carbon atom, with the proviso that the diphosphine ligand is not 1,2-P,P'bis-(9-phosphabicyclononyl) benzene.

Preferences for the ligands are as described herein-before.

In a preferred embodiment the diphosphine ligand comprises a cycloalkene as described hereinbefore, and accordingly this invention also provides a diphosphine ligand having the general formula (III):

$$X^1-R^3-X^2 \quad (III)$$

wherein $X^1$ and $X^2$ each independently represent an optionally substituted cyclic group with at least 5 ring atoms, of which one is a phosphorus atom, and $R^3$ represents a bivalent cycloalkene group which is connected to each phosphorus atom by a sp² hybridized carbon atom.

Preferences for the ligands are as described herein-before.

In another preferred embodiment the diphosphine ligand comprises an aromatic group containing one or more heteroatoms as a ring atom as described hereinbefore, and accordingly this invention also provides a diphosphine ligand having the general formula (IV)

$$X^1-R^4-X^2 \quad (IV)$$

wherein $X^1$ and $X^2$ each independently represent an optionally substituted cyclic group with at least 5 ring atoms, of which one is a phosphorus atom, and $R^4$ represents a bivalent aromatic group, wherein the aromatic ring contains one or more hetero atoms as a ring atom, which aromatic group is connected to each phosphorus atom by a sp² hybridized carbon atom Preferences for the ligands are as described herein-before.

The ligands can suitably be prepared as indicated in the examples, e.g. by reacting 9-phosphabicyclononane with the appropriate dihalo-bridging group. The 9-phosphabicyclononane can conveniently be prepared as described by Elsner et al. (Chem. Abstr. 1978, vol. 89, 180154x)<The isomerically pure 9-phosphabicyclononane (>95% wt) can conveniently be obtained as described in WO 02/064250.

The invention further provides a catalyst comprising:

(a) a source of Group VIII metal cations; and (b) a diphosphine ligand as described hereinabove.

Suitable Group VIII metals include the metals rhodium, nickel, palladium and platinum. Of these, palladium and platinum are preferred.

Examples of suitable metal sources are platinum or palladium compounds such as salts of palladium or platinum and nitric acid, sulphuric acid or sulphonic acids, salts of platinum or palladium and carboxylic acids with up to 12 carbon atoms, palladium- or platinum complexes, e.g. with carbon monoxide or acetylacetonate, or palladium or platinum combined with a solid material such as an ion exchanger Palladium(II) acetate and platinum(II) acetylacetonate are examples of preferred metal sources.

In the catalyst systems of the invention, any acid having a $pK_a<3$, measured in an aqueous solution at 18° C. or any salt derived thereof can be used.

As used herein, the term $pK_a$ is the negative logarithm of the equilibrium constant $K_a$, i.e. $pK_a=-\log K_a$, wherein for any acid HA which partially dissociates in solution, the equilibrium HA=H⁺A⁻ is defined by an equilibrium constant $K_a$, where $$K_a = \frac{[H^+][A^-]}{[HA]}$$

Sulphonic acids are preferred. Suitable sulphonic acids include sulphonic acids comprising one or more halogen atoms, such as F, Cl, Br and I. Examples of suitable sulphonic acids include therefore methanesulphonic acid, fluoro-methanesulphonic acid, trichloro-methanesulphonic acid, trifluoro-methanesulphonic acid, tert-butane-sulphonic acid, p-toluenesulphonic acid and 2,4,6-trimethyl-benzene-sulphonic acid.

In addition the presence of a source of halide is required. Suitable sources of halide include halide salts, preferably salts of alkali metals, such as for example NaI, NaCl, NaBr, KCl; and hydrogen halides such as HI, HCl, HBr, or HF. Of these HI, HCl and HBr are preferred and HCl is most preferred.

The ethylenically unsaturated compound, used as starting material, is preferably an ethylenically unsaturated compound having from 2 to 40 carbon atoms per molecule, or a mixture thereof. Preferred are compounds having from 2 to 30 carbon atoms, or mixtures thereof, The advantages of the process according to the invention are further especially pronounced for larger ethylenically unsaturated compounds comprising at least 4 carbon atoms, and preferably at least 6 carbon atoms. More preferably such a large ethylenically unsaturated compound comprises 8 or more carbon atoms, preferably from 8 to 25 and more preferably from 8 to 18 carbon atoms. Alkenes are preferred, particularly those with at least 4 carbon atoms. The ethylenically unsaturated compound can further be a straight carbon chain or can be branched. Suitable ethylenically unsaturated compounds hence include substituted compounds. Preferably such substituents are alkyl groups, preferably alkyl groups comprising from 1 to 6, more preferably from 1 to 4 carbon atoms, such as methyl, ethyl, n-propyl, isopropyl, n-butyl, iso-butyl and tert.-butyl. Examples of suitable ethylenically unsaturated compounds include ethene, propene, butene, pentene, 1-hexene, internal hexenes, 1-heptene, internal heptenes, 1-octene, internal octenes, 1-nonene or internal nonenes, 1-decene or internal decenes, undecenes, methyl-branched undecenes, dodecenes, methyl-branched dodecenes, methyl-substituted or unsubstituted $C_{13}$, $C_{14}$ or $C_{15}$-olefins and mixtures of those.

The process is further especially suitable for the hydroformylation of mono-alkenes in the presence of dienes. Without wishing to be bound to any kind of theory, it is thought that the presence of dienes slows down the activity of the catalyst system. As shown in the examples, in the process according to the invention high activities are even obtained when a mixture of mono-alkenes and dienes is used as a substrate.

The process according to the invention is hence especially suitable for the hydroformylation of, for example, octenes in a mixture of octenes, octadienes, methyl-heptadienes and/or dimethyl-hexadienes.

The ethylenically unsaturated compound can further be an ethylenically unsaturated compound comprising functional groups or heteroatoms, such as nitrogen, sulphur or oxide Examples include unsaturated carboxylic acids, esters of such acids or alkene nitrites. Suitable ethylenically unsaturated comprising functional groups or heteroatoms include for example pentene nitrites and methyl-pentenoates Preferably, however, the ethylenically unsaturated compound does not comprise any functional groups or heteroatoms and is an olefin comprising only carbon atoms.

In the process of the invention, the unsaturated starting material and the formed product may act as reaction diluent. Hence, the use of a separate solvent is not necessary. Conveniently, however, the hydro-formylation reaction may be carried out in the additional presence of a solvent. As such, saturated hydrocarbons, e.g. paraffins and isoalkanes are recommended and furthermore saturated hydrocarbons, preferably having from 4 to 10 carbon atoms per molecule; ethers such as 2,5,8-trioxanonane (diglyme), diethylether and anisole, and ketones, such as methylbutylketone. Solvents, comprising or substantially consisting of sulphones are also preferred. Sialphones are in particular preferred, for example dialkylsulphones such as dimethylsulphone and diethylsulphone and cyclic sulphones, such as sulfolane (tetrahydrothiophene-2,2-dioxide), 2-methylsulfolane and 2-methyl-4-ethylsulfolane.

In a preferred embodiment mixtures of sulphones and alkanols and/or water are used as a solvent. Suitable alkanols that can be used in such a solvent mixture include monoalkanols and polyalkanols. Preferably mono-alkanols having from 1 to 20, more preferably from 4 to 12 carbon atoms are used. The alkanol can be a straight alkanol or it can be branched. Preferably the alkanol is branched and the main carbon chain of the alkanol is substituted with one or more alkyl groups, preferably alkyl groups comprising from 1 to 6, more preferably from 1 to 4 carbon atoms such as methyl, ethyl, n-propyl, isopropyl, n-butyl, iso-butyl and tert.-butyl. Examples of suitable alkanols include methyl-pentanol, methyl-hexanol, ethyl-hexanol, methyl-heptanol, ethyl-heptanol, dimethylhexanolr dimethylheptanol and methyl-octanol. Most preferably, however, the alkanol is the alkanol which is obtained when the ethylenically unsaturated compound is hydroformylated and subsequently hydrogenated. A solvent mixture preferably contains in the range from about 0.1 to about 10, more preferably in the range from about 0.5 to about 5 ml of alkanol per ml of sulphone; and, if present, in the range from about 0.001 to about 1, more preferably in the range from about 0.01 to about 0.5 ml of water per ml of sulphone.

The quantity in which the catalyst system is used, is not critical and may vary within wide limits. Usually amounts in the range of about $10^{-8}$ to about $10^{-1}$, preferably in the range of about $10^{-7}$ to about $10^{-2}$ mole atom of Group VIII metal per mole of ethylenically unsaturated compound are used. The amounts of the participants in the catalyst system are conveniently selected such that per mole atom of Group VIII metal from about 0.1 to about 10, preferably from about 0.5 to about 6, and more preferably from about 1 to about 3 moles of bidentate diphoshine are used; from about 0.1 to about 15, preferably from about 0.5 to about 10, and more preferably from about 1 to about 6 moles of anion source or a complex anion source. The hydrogen halide should be present in a ratio of about 0.01 to about 100 mmol hydrogen halide to about 1 mmol Group VIII metal. More preferably the hydrogen halide is present in the range from about 0.1 to about 10 and most preferably in the range of about 0.5 to about 5 mol per mol of Group VIII metal is present.

Carbon monoxide partial pressures in the range of about 1-65 bar are preferred. In the process according to the present invention, the carbon monoxide can be used in its pure form or diluted with an inert gas such as nitrogen, carbon dioxide or noble gases such as argon.

For hydroformylation the coreactant can be molecular hydrogen, or more generally a hydride source. The carbon monoxide and hydrogen are preferably supplied in a molar ratio of hydrogen to carbon monoxide within the range of about 10:1 to about 1:5, preferably about 6:1 to about 1:3. The molar ratio of hydrogen to carbon monoxide can influence the type of product prepared. When the desired product is an alkanol, an excess of hydrogen is needed to enable the hydrogenation of the originally formed aldehyde or ketone. Therefore, if the desired product is an alkanol, preferably a molar ratio of hydrogen to carbon monoxide within the range of about 4:1 to about 1.5:1 is used.

The hydroformylation can be suitably carried out at moderate reaction conditions. Hence temperatures in the range of about 50 to about 200° C. are recommended, preferred temperatures being in the range of about 70 to about 160° C. Reaction pressures in the range of about 5 to about 150 bar are preferred, lower or higher pressures may be selected, but are not considered particularly advantageous. Moreover, higher pressures require special equipment provisions.

The invention will be illustrated by the following non-limiting examples.

EXAMPLE 1

Preparation of
1,2-PP'bis(9-phosphabicyclo[3.3.1]nonyl)) benzene

A 300 ml Schlenk vessel under nitrogen atmosphere is charged with 9.44 g (40 mmol) of 1,2-dibromobenzene, 22.4 g (200 mmol) of 1,4-diazabicyclo[2,2,2]octane, 13 g (91 mmol) of 9-phosphabicyclo[3.3.1]nonane, 2.32 g (2 mmol) of tetrakis(triphenylphosphine)palladium(0) and 150 ml of xylene (solvent). The mixture is stirred overnight at 140° C., during which period a precipitate of 1,4-diazabicyclo[2,2,2] octane hydrogenbromide is formed. After cooling to 100° C. the mixture is filtered hot. Upon cooling of the xylene solution, crystals of 1,2-bis-([3.3.1]-9-phosphabicyclononane) benzene are formed. The liquid is decanted, and the product recrystallized from 100 ml of hot toluene. 1,2-bis(9-phosphabicyclo[3.3.1]nonyl) benzene is obtained in a yield of 7.1 g (20 mmol, 50%), pure according to 31p and $^1$H NMR, 31P NMR ($CD_2Cl_2$): −16.6 ppm $^1$H NMR ($CD_2Cl_2$): 7.15 ppm (m, 2H), 7.10 ppm (m, 2H), 2.63 ppm (s, 4H), 12-2.2 ppm (m, 24H)

EXAMPLE 2

Preparation of
1,2-PP'bis(9-phosphabicyclo[3.3.1]nonyl) cyclopentene

A 200 ml Schlenk vessel under nitrogen atmosphere is charged with 5.0 g (22 mmol) of 1,2-dibromocyclopentene, 9.0 g (80 mmol) of 1,4-diazabicyclo[2,2,2]octane, 8.0 g (56 mmol) of 9-phosphabicyclo[3.3.1]nonane, 1.16 g (1 mmol) of tetrakis(triphenylphosphine)palladium(0) and 60 ml of xylene. The mixture is stirred overnight at 140° C., during which period a precipitate of 1,4-diazabicyclo[2,2,2]octane hydrogenbromide is formed. After cooling to 100° C. the mixture is filtered hot. Upon cooling of the xylene solution, a precipitate of 1,2-PP'bis(9-phosphabicyclo[3.3.1]nonyl)cyclopentene is formed. After further cooling to −35° C., the liquid is decanted and the residue purified by stirring with hot methanol. 1,2-PP'bis(9-phosphabicyclo[3.3.1]nonyl) cyclopentene is obtained in a yield of 4.3 g (12.4 mmol, 56%), pure according to $^{31}$P and $^1$H NMR. $^{31}$P NMR(CD$_2$Cl$_2$): −25.9 ppm $^1$H NMR (CD$_2$Cl$_2$): 2.60 ppm (m, 4H), 2.26 ppm (m, 4H), 1.4-2.1 ppm (m, 24H).

EXAMPLE 3

Preparation of
3,4-PP'bis(9-phosphabicyclo[3.3.1]nonyl) thiophene 3,4-PP'bis(9-phosphabicyclo[3.3.1]nonyl) thiophene is prepared from 3,4-dibromothiophene in a similar way as 1,2-PP'bis(9-phosphabicyclo[3.3.1]nonyl)cyclopentene is prepared from 1,2-dibromopentene. 3,4-PP'bis(9-phospha-bicyclo[3.3.1]nonyl)thiophene is obtained in a yield of 40%, pure according to $^{31}$P NMX (CD$_2$Cl$_2$): −24.4 ppm $^1$H NMR (CD$_2$Cl$_2$): 7.08 ppm (s, 2H), 2.46 ppm (s, 4H), 1.4-2.2 ppm (m, 24H).

IN EXAMPLES 1-14 AND COMPARATIVE EXAMPLES A-H

BPEE=1,2-PP'bis(9-phosphabicyclo[3.3.1]nonyl) benzene
BPCP=1,2-PP'bis(9-phosphabicyclo[3.3.1]nonyl) cyclopentene
BPTH=3,4-PP'bis(9-phosphabicyclo[3.3.1]nonyl) thiophene
BPET=1,2-PP'bis(9-phosphabicyclo[3.3.1]nonyl)ethane
BPPT=1-P(9-phosphabicyclo[3.3.1]nonyl),2-P(9-phospha-bicyclo[3.3.1]nonyl-methyl) benzene
BPF=1,2-PP'bis(9-phosphabicyclo[3.3.1]nonyl) 4,5-difluoro-benzene
BPBU=2,3-PP'bis(9-phosphabicyclo[3.3.1]nonyl) butane
BPCH=1,2-PP'bis(9-phosphabicyclo[3.3.1]nonyl)cyclohexane
MSA=methane sulfonic acid
FSA=trifluoromethane sulfonic acid

EXAMPLES 4-8, COMPARATIVE EXAMPLES A-D; HYDROFORMYLATION

Examples 4-8 and Comparative Examples A-D were carried out in a 350 ml magnetically stirred autoclave The autoclave was charged with a substrate as indicated in Table I, 30 ml of ethylhexanol, 10 ml sulfolane and 0.5 ml of water, 0.25 mmol (56 mg) of Palladium (II) acetate, an amount of a bidentate diphosphine as indicated in Table I, and an amount of acid as indicated in Table I. After being flushed with nitrogen, the auto-clave was pressurized with carbon monoxide to a partial pressure of 20 bar and hydrogen to a partial pressure of 40 bar. Subsequently, the reactor was sealed and the contents were heated to a temperature as indicated in Table I and maintained at that temperature for 5 hours. In Table I the initial rate of carbonylation is indicated (in react. rate). The initial rate of carbonylation is defined as the mean rate of carbon monoxide consumption over the first 30% substrate conversion. After cooling, a sample was taken from the contents of the reactor and analysed by Gas Liquid Chromatography. The percentage alkanol product, based on the total amount of product, is indicated in Table I. The percentage linear alkanol product, based on the total amount of alkanol product, is also indicated in Table I. The remainder comprised mainly aldehydes and ketones and acetals, which are intermediate products to alkanols. Furthermore some hydrogenation byproduct was obtained. The amount of hydrogenation byproduct is indicated in Table I. The experiments in Table I indicate that the catalyst according to the invention is more active towards a hydroformylation product than some prior art catalysts.

TABLE I

| Example | Substrate (ml) | bidentate diphosphine (mmol) | acid (mmol) | T (°C.) | in. react. rate (mol/mol Pd/hr) | alkanol product (%) | linear alkanol product (%) | Hydrogenation byproduct (%) |
|---|---|---|---|---|---|---|---|---|
| 4 | 1-octene (20) | BPBE (0.4) | MSA (1), HCl (0.2) | 120 | 1380 | >99 | 68 | <1 |
| 5 | 1-octene (20) | BPBE (0.4) | MSA (0.5) HCl (0.1) | 120 | 920 | >99 | 65 | <1 |
| 6 | 1-octene (20) | BPBE (0.4 | FSA (0.5) HCl (0.2) | 110 | 680 | >99 | 72 | <1 |
| A | 1-octene (20) | BPBE (0.4) | MSA (0.5) | 120 | 156 | 75 | 63 | <1 |
| B | 1-octene (30) | BPBU (0.4) | MSA (0.5) HCl (0.1) | 105 | 119 | 75 [1]) | 58 | 4.2 |
| 7 | internal C11, C$_{12}$ olefin (30) | BPBE (0.5) | FSA (1) HCl (0.2) | 115 | 1061 | >99 | 75 | <1 |
| C | internal C11, C$_{12}$ olefin (30) | BPET (0.5) | FSA (1) HCl (0.2) | 115 | 156 | 90 | 73 | <1 |
| 8 [2]) | internal C11, C$_{12}$ olefin (30) | BPCP (0.5) | FSA (1) HCl (0.2) | 115 | 1206 | >99 | 71 | <1 |
| 9 | internal C11, C$_{12}$ olefin (30) | BPTH (0.4) | FSA (0.5) HCl (0.2) | 115 | 1397 | >99 | 77 | <1 |
| D | internal C11, C$_{12}$ olefin (30) | BPCH (0.4) | FSA (0.5) HCl (0.2) | 120 | 307 | 88 | 76 | <1 |

[1]) Also esters are formed as a byproduct here.
[2]) Carried out in the presence of 50 μl 2,5-dimethyl-2,4-hexadiene.

EXAMPLE 10, COMPARATIVE EXAMPLE E; DEMONSTRATION OF DIENE TOLERANCE

Example 10 and Comparative Example R were carried out in a 350 ml magnetically stirred autoclave. The autoclave was charged with 30 ml of an mixture of internal $C_{11}$ and $C_{12}$ olefins (as substrate), 30 ml of ethylhexanol, 10 ml sulfolane and 0.5 ml of water, 0.25 mmol (56 mg) of Palladium (II) acetate, an amount of a bidentate di-phosphine as indicated in Table 1, 0.2 mmol HCl and an amount of sulfonic acid as indicated in Table II. In addition 0.25 ml 2,5 dimethyl-2,4 hexadiene was added to the autoclave. After being flushed with nitrogen, the autoclave was pressurized with carbon monoxide to a partial pressure of 20 bar and hydrogen to a partial pressure of 40 bar. Subsequently, the reactor was sealed and the contents were heated to a temperature of 135° C. and maintained at that temperature for 5 hours. In Table II the initial rate of carbonylation is indicated (in. react. rate). The initial rate of carbonylation is defined as the mean rate of carbon monoxide consumption over the first 30% substrate conversion. After cooling, a sample was taken from the contents of the reactor and analysed by Gas Liquid Chromatography. The percentage alkanol product, based on the total amount of product, is indicated in Table II. The percentage linear alkanol product, based on the total amount of alkanol product, is also indicated in Table II. Furthermore some hydrogenation byproduct was obtained. The amount of hydrogenation byproduct is indicated in Table II. The experiments in Table II indicate that the process according to the invention is more tolerant towards a feed containing dienes.

autoclave was charged with 15 ml of methylpentenoate, 0.25 mmol (56 mg) of Palladium II acetate, 10 ml sulfolane, an amount of methanol as indicated in Table III, an amount of a bidentate diphosphine as indicated in Table III, an amount of hydrochloric acid (HCl) as indicated in Table III, and an amount of an sulfonic acid as indicated in Table III. After being flushed with nitrogen, the autoclave was pressurized with carbon monoxide to a partial pressure of 20 bar and hydrogen to a partial pressure of 40 bar. Subsequently, the reactor was sealed and the contents were heated to a temperature as indicated in Table III and maintained at that temperature for 5 hours. After cooling, a sample was taken from the contents of the reactor and analysed by Gas Liquid Chromatography. The reaction rate towards the hydroformylation products is indicated in Table III. This reaction rate is calculated by dividing the moles formed hydroformylation product as determined by Gas Liquid Chromatography, by the moles of palladium and the time (hours) required for 100% conversion.

The hydroformylation products include 6-hydroxy-methylhexanoate, 5-hydroxy-4-methyl-methylpentanoate and 4-hydroxy-3-ethyl-methylbutanoate. The selectivity towards the desired linear 6-hydroxy methyl hexanoate, based on the

TABLE II

| Example | Bidentate diphosphine (mmol) | sulfonic acid (mmol) | in. react. rate (mol/mol Pd/hr) | alkanol product (%) | linear alkanol product (%) | Hydrogenation product (%) |
|---|---|---|---|---|---|---|
| 10 | BPBE (0.4) | FSA (0.5) HCl (0.2) | 680 | 99 | 73 | 0.4 |
| E | BPET (0.4) | FSA (0.5) HCl (0.2) | 25 | 75 | 70 | 0.6 |

EXAMPLES 11-14, COMPARATIVE EXAMPLES F AND G; PENTENOATE HYDROFORMYLATION

Examples 11-14 and Comparative Examples F and G were carried out in a 350 ml magnetically stirred autoclave. The total amount of hydroformylation product is indicated as the linearity in Table III. Part of the substrate was converted to methylpentanoate in a competing hydrogenation reaction. The percentage methylpentanoate byproduct prepared is indicated in Table III. These experiments show that in the process according to the invention also high reaction rates towards a hydroformylation product of pentenoates can be obtained

TABLE III

| Example | methanol (ml) | Bidentate diphosphine (mmol) | HCl (mmol) | sulfonic acid (mmol) | T (° C.) | activity [3]) (mol/mol Pd/hr) | linearity (%) | methyl-pentanoate (%) |
|---|---|---|---|---|---|---|---|---|
| 11 | 40 | BPCP (0.4) | 0.5 | FSA (0.5) | 115 | 2600 | 73 | 22 |
| 12 | 50 | BPBE (0.4) | 0.5 | FSA (0.5) | 115 | 900 | 67 | 21 |
| 13 | 50 | BPTH (0.4) | 0.5 | FSA (0.5) | 115 | 1500 | 70 | 19 |
| F | 50 | BPET (0.4) | 0.5 | FSA (0.5) | 115 | 500 | 68 | 77 |
| G | 50 | BPPT (0.4) | 0.5 | FSA (0.5) | 115 | 450 | 38 | 74 |
| 14 | 50 | BPFB (0.4) | 0.5 | FSA (0.5) | 115 | 920 | 64 | 18 |

[3]) activity towards hydroformylation products

We claim:

1. A diphosphine ligand having the general formula (III):

$$X^1\text{—}R^3\text{—}X^2 \quad (III)$$

wherein $X^1$ and $X^2$ each independently represent an optionally substituted cyclic group with at least 5 ring atoms, of which one is a phosphorus atom, and $R^3$ represents a bivalent cycloalkene group which is connected to each phosphorus atom by a $sp^2$ hybridized carbon atom.

2. A catalyst comprising:
   (a) a source of Group VIII metal cations; and
   (b) the diphosphine ligand of claim 1.

* * * * *